(12) United States Patent
Rathinasabapathi et al.

(10) Patent No.: US 8,519,226 B2
(45) Date of Patent: Aug. 27, 2013

(54) INCREASED STRESS TOLERANCE, YIELD, AND QUALITY VIA GLUTAREDOXIN OVEREXPRESSION

(75) Inventors: Bala Rathinasabapathi, Gainesville, FL (US); Sabarinath Sundaram, College Station, TX (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 246 days.

(21) Appl. No.: 12/996,884

(22) PCT Filed: Jul. 16, 2009

(86) PCT No.: PCT/US2009/050820
§ 371 (c)(1),
(2), (4) Date: Jan. 3, 2011

(87) PCT Pub. No.: WO2010/021798
PCT Pub. Date: Feb. 25, 2010

(65) Prior Publication Data
US 2011/0131681 A1    Jun. 2, 2011

Related U.S. Application Data (60) Provisional application No. 61/090,643, filed on Aug. 21, 2008.

(51) Int. Cl.
| | |
|---|---|
| *C12N 15/82* | (2006.01) |
| *C12N 9/02* | (2006.01) |
| *C07K 14/415* | (2006.01) |
| *A01H 5/00* | (2006.01) |

(52) U.S. Cl.
USPC ........... 800/289; 800/278; 800/290; 800/295; 435/189

(58) Field of Classification Search
None
See application file for complete search history.

(56) References Cited

U.S. PATENT DOCUMENTS

| | | | |
|---|---|---|---|
| 5,792,506 | A | 8/1998 | Buchanan et al. |
| 6,084,070 | A | 7/2000 | Hillman et al. |
| 6,414,222 | B1 | 7/2002 | Gengenbach et al. |
| 6,583,271 | B1 | 6/2003 | Buchanan et al. |
| 6,756,525 | B1 | 6/2004 | Murata |
| 2004/0052774 | A1 | 3/2004 | Creissen |
| 2005/0260739 | A1 | 11/2005 | Rosen et al. |
| 2006/0075522 | A1 | 4/2006 | Cleveland et al. |
| 2006/0205598 | A1 | 9/2006 | Moon |
| 2007/0006349 | A1 | 1/2007 | Patell |
| 2007/0180585 | A1 | 8/2007 | Rathinasabapathi et al. |

FOREIGN PATENT DOCUMENTS

| | | |
|---|---|---|
| CN | 1614020 | 5/2005 |
| CN | 1844377 | 10/2006 |
| WO | WO2007030001 | 3/2007 |

OTHER PUBLICATIONS

Jonak et al. Stress signaling in plants: A mitogen-activated protein kinase pathway is activated by cold and drought. PNAS. 93: 11274-11279.*
Schuzle. et al. Environment as stress factor: Stress physiology of plants. Plant Ecology. Springer. 2005. pp. 7-11.*
Sundaram et al. An arsenate-activated glutaredoxin from the arsenic hyperaccumulator fern *Pteris vitta* L. regulates intracellular arsenite. Journal of Biological Chemistry. 2008. 283(10) 6095-6101.*
Jonak et al. Stress signaling in plants: A mitogen-activated protein kinase pathway is activated by cold and drought. PNAS. 1996. 93: 11274-11279.*
Handberg et al. *Lotus japonicus*, an autogamous, diploid legume species for classical and molecular genetics. The Plant Journal. 1992. 2(4): 487-496.*
"Sundaram S, Rathinasabapathi B (2010) Transgenic expression of fern *Pteris vittata* glutaredoxin PvGrx5 in *Arabidopsis thaliana* increases plant tolerance to high temperature stress and reduces oxidative damage to proteins. Planta 231:361-369".
Sundaram, et al. An arsenate-activated Glutaredoxin from the Arsenic Hyperaccumulator Fern *Pteris vittala* L. Regulates Intracellular Arsenite, *J. Biol. Chem* (Mar. 7, 2008) vol. 283, No. 10, p. 6095/6101, p. 6095, col. 2, para 4, in 5; p. 6100, col. 1, para 4, in 8—col. 2, in 1; title.
"Glutathione transferases in the genomics era: New insights and perspectives," Carla Frova, *Biomolecular Engineering* 23 (2006) 149-169.
Redox sensing and signaling associated with reactive oxygen in chloroplasts, peroxisomes and mitochondria, Foyer et al. *Physiologia Plantarum* 119: 355-364 2003.

* cited by examiner

*Primary Examiner* — Shubo (Joe) Zhou
*Assistant Examiner* — Ashley K Buran
(74) *Attorney, Agent, or Firm* — Timothy H. Van Dyke; Beusse, Wolter, Sanks, Mora & Maire, P.A.

(57) ABSTRACT

Oxygenic photosynthesis is the major site of production of reactive oxygen species (ROS). Under high temperature stress, increased ROS damage the photosynthetic machinery, membranes and proteins of plants. The present invention is directed to methods for increasing the stress tolerance of plants by expressing PvGrx5 in the plants.

5 Claims, 8 Drawing Sheets

A

>gi|124110116|gb|EF052272.1| Pteris vittata glutaredoxin mRNA, complete cds
CGGCCGGGGGAGAGAGAGAGAGAGAGAGACCAAGCTATGGCGTCCAGGGCCGTGCAAACGAGTGTT
GGGCTTCTGGGCGGCAGCGACCTCCACTCCTCTTCTACTTCCACAAACAATTTTCAATCCTTGCTCTCCT
TCTCGCCCACTTTTCTTCTGTCAAAAAGAGCCACTGTGCTCTCGAGCACCCAGCACCGTCCGAGTTGGAC
AACTGCGCAGCCGCCCAACAGACTCGTGTGTCGATCCAGCTATGGTGGTGCCCCAACTGGTTTGTCACCG
GAATTGAAAGAAGCTGTAGACAAGTTTGTAACGTCCAACAAGGTGGTGCTGTTCATGAAGGGTACCAAGT
TGTTTCCTCAGTGTGGATTTTCAAATACTGTGGTACAAATACTGAATTCACTGAATGTTCCTTATGAGAC
GGTAAACATTCTGGAGAACGAGCAAATGCGCTATGCCATGAAAATTTACTCCAGCTGGCCCACGTTTCCT
CAGCTTTATGTAGATGGAGAATTTTTTGGTGGTTGCGACATTACACTGGAGGCATTCAAGAACGGGGAGC
TACAGGAAGCAATCGAGAAGGCAATGTGCTCGTAGAATTGGGGCATTTGATGTATCATGCACTTAAATAC
AAAGGTGTAATATAGATTGTTTCGAAATTCGATTTGTTGGTAGCTGCAATTCCAGTGTAAGGAAGATGA
ATGTATTTCAAGGCGTGTGTTTGATGGTAAAAGAAAAAAAAAAAAAAAAAAAAAAAAAAAAAA (SEQ ID
NO.1)

B

>gi|124110117|gb|ABM91435.1| glutaredoxin [Pteris vittata]
MASRAVQTSVGLLGGSDLHSSTSTNNFQSLLSPSPTPLLSKRATVLSSTQHRPSWTTAQPPNRLVCRSS
YGGAPTGLSPELKEAVDKFVTSNKVVLFMKGTKLFPQQGFSNTVVQILNSLNVPYETVNILENEQMRYAM
KIYSSWPTPPQLYVDGEFFGGCDITLEAFKNGELQEAIEKAMCS (SEQ ID NO. 2)

SEQUENCE LISTING

```
<160> NUMBER OF SEQ ID NOS: 2

<210> SEQ ID NO 1
<211> LENGTH: 763
<212> TYPE: DNA
<213> ORGANISM: Pteris vittata

<400> SEQUENCE: 1
cggccggggg agagagagag agagagagag agaccaagct atggcgtcca gggccgtgca      60
aacgagtgtt gggcttctgg gcggcagcga cctccactcc tcttctactt ccacaaacaa     120
ttttcaatcc ttgctctcct tctcgcccac ttttcttctg tcaaaaagag ccactgtgct     180
ctcgagcacc cagcaccgtc cgagttggac aactgcgcag ccgcccaaca gactcgtgtg     240
tcgatccagc tatggtggtg ccccaactgg tttgtcaccg gaattgaaag aagctgtaga     300
caagtttgta acgtccaaca aggtggtgct gttcatgaag ggtaccaagt tgtttcctca     360
gtgtggattt tcaaatactg tggtacaaat actgaattca ctgaatgttc cttatgagac     420
ggtaaacatt ctggagaacg agcaaatgcg ctatgccatg aaaatttact ccagctggcc     480
cacgtttcct cagctttatg tagatggaga atttttggt ggttgcgaca ttacactgga     540
ggcattcaag aacggggagc tacaggaagc aatcgagaag gcaatgtgct cgtagaattg     600
gggcatttga tgtatcatgc acttaaatac aaaggtgtaa tatagattgt ttcgaaattg     660
gatttgttgg tagctgcaat ttccagtgta aggaagatga atgtatttca aggcgtgtgt     720
ttgatggtaa aagaaaaaaa aaaaaaaaaa aaaaaaaaa aaa                        763

<210> SEQ ID NO 2
```

```
<211> LENGTH: 184
<212> TYPE: PRT
<213> ORGANISM: Pteris vittata

<400> SEQUENCE: 2

Met Ala Ser Arg Ala Val Gln Thr Ser Val Gly Leu Leu Gly Gly Ser
1               5                   10                  15

Asp Leu His Ser Ser Ser Thr Ser Thr Asn Asn Phe Gln Ser Leu Leu
            20                  25                  30

Ser Phe Ser Pro Thr Phe Leu Leu Ser Lys Arg Ala Thr Val Leu Ser
            35                  40                  45

Ser Thr Gln His Arg Pro Ser Trp Thr Thr Ala Gln Pro Pro Asn Arg
        50                  55                  60

Leu Val Cys Arg Ser Ser Tyr Gly Gly Ala Pro Thr Gly Leu Ser Pro
65                  70                  75                  80

Glu Leu Lys Glu Ala Val Asp Lys Phe Val Thr Ser Asn Lys Val Val
                85                  90                  95

Leu Phe Met Lys Gly Thr Lys Leu Phe Pro Gln Cys Gly Phe Ser Asn
            100                 105                 110

Thr Val Val Gln Ile Leu Asn Ser Leu Asn Val Pro Tyr Glu Thr Val
        115                 120                 125

Asn Ile Leu Glu Asn Glu Gln Met Arg Tyr Ala Met Lys Ile Tyr Ser
    130                 135                 140

Ser Trp Pro Thr Phe Pro Gln Leu Tyr Val Asp Gly Glu Phe Phe Gly
145                 150                 155                 160

Gly Cys Asp Ile Thr Leu Glu Ala Phe Lys Asn Gly Glu Leu Gln Glu
                165                 170                 175

Ala Ile Glu Lys Ala Met Cys Ser
            180
```

INCREASED STRESS TOLERANCE, YIELD, AND QUALITY VIA GLUTAREDOXIN OVEREXPRESSION

RELATED APPLICATION

This application claims priority to U.S. Ser. No. 61/090,643 filed Aug. 21, 2008, which is incorporated herein in its entirety.

STATEMENT REGARDING FEDERALLY SPONSORED DEVELOPMENT

Development for this invention was supported in part by Contract No. 2005-34135-15898, awarded by the United States Department of Agriculture (USDA-T-STAR Program). Accordingly, the United States Government may have certain rights in this invention.

FIELD OF THE INVENTION

The present invention provides methods and compositions for increasing the tolerance of a plant to biotic and abiotic stresses (i.e. high temperature stress and drought) and for reducing oxidative damage to proteins of the plant.

BACKGROUND OF THE INVENTION

High temperature stress is a major limiting factor for plant growth and crop productivity. Models suggest that global warming has substantial negative effects on the world production of major grains wheat, maize and barley, as well as important dicot plants (Lobell and Field, 2007). Between 1970 and 2007, 78 weather-related disasters with damages equal to or exceeding $1 billion were recorded in the U.S. alone. Among these, at least 12 vents were due to drought and heat waves, totaling $106 billion in estimated damage, with significant losses to agriculture (Ross and Lott, 2003 and source: lwf.ncdc.noaa.gov/oa/reports/billion z). Despite the great economic importance of drought and high temperature stress to agriculture, little progress has been made in breeding stress-tolerant cultivars, partly due to the complex nature of these stresses and plant adaptations to such stresses. A major component of heat stress has been Several members of the plant protein networks in heat stress response, including heat shock proteins (HSPs), heat stress transcription factors (HSFs) and antioxidant enzymes, have been studied using mutants, transgenic lines and transcriptome analyses (Koskull-Doring et al. 2007; Kotak et al. 2007; Mittler, 2005). However, enzymes protecting specific target proteins from oxidative damage have not been investigated for their possible role in stress tolerance.

BRIEF DESCRIPTION OF THE DRAWINGS

The invention is explained in the following description in view of the drawings that show:

FIG. 6 shows PvGrx5-expressing *Arabidopsis thaliana* lines were less affected by heat stress relative to control plants. (A) Injury index calculated from ion leakage from leaf tissue. Bars represent means and standard errors (n=7) and those noted with same letters are not significantly different at $P<0.05$ by Duncan's multiple range test. (B) Thiobarbituric acid reactive substances (TBARS) in leaves under control (open bars) and heat stress (closed bars) conditions. (C) Carbonyl content of leaf proteins under control (open bars) and heat stress (closed bars) conditions. Wild-type is WT, Vector control is R5, and PvGRX5-expressing lines are SG2-B, SG2-7 and SG2-1. Bars represent means and standard errors (n=5) and those noted with same letters are not significantly different at $P<0.05$ by Duncan's multiple range test.

FIG. 8. PvGrx5-expressing transgenic lines are more tolerant to drought stress than wild-type and vector control line.

(A) Morphology of vector control and SG2-7 and SG2-1 PvGrx-5 lines immediately photographed after 10 days of drought imposed by stopping irrigation. (B) Above ground biomass per plant following 10 d of drought and (C) Photosynthetic efficiency based on PSII chlorophyll fluorescence measurements for PvGrx-5 expressing lines SG2-7 and SG2-1 compared to vector control.

DETAILED DESCRIPTION OF THE INVENTION

Oxygenic photosynthesis is the major site of production of reactive oxygen species (ROS). Under high temperature stress, increased ROS damage the photosynthetic machinery, membranes and proteins (Sharkey, 2005). This, in turn, leads to stunted growth of the plants, lower crop yield, lower biomass, and even death of the plant. The present inventors have surprisingly found that plants, i.e. *Arabidopsis thaliana* transgenic lines, expressing PvGrx5, a glutaredoxin of fern *Pterris vittata*, are more tolerant to stress, including heat stress and drought, as well as show reduced damage due to oxidative stress. Accordingly, the present invention provides methods for increasing biotic and abiotic stress tolerance of plants and for reducing oxidative damage by expressing PvGrx5 in plants or plant cells.

Unless otherwise defined, all technical and scientific terms used herein have the same meaning as commonly understood by one of ordinary skill in the art of molecular biology. Pv5-6 represents the cDNA isolated from *Pteris vittata*, PvGRX5 refers to the encoded protein and the abbreviation Grx is for glutaredoxin. Homozygous transgenic lines expressing vector control are referred as R5 lines, those expressing PvGRX5 as SG2 lines and wild-type as WT throughout this document. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

As used herein, the term "enhancement" means increasing the intracellular activity of one or more enzymes in a plant cell and/or plant which are encoded by the corresponding DNA. Enhancement can be achieved with the aid of various manipulations of the plant cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes, which are incorporated upstream of the structural gene, act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

It should be noted that the present invention also encompasses the utilization of nucleotide sequences (and the corresponding encoded proteins) having sequences comprising or complementary to at least about 80%, preferably at least about 85%, more preferably at least about 90%, and most preferably at least about 95% of the nucleotides in sequence (i.e., having sequence identity to) SEQ ID NO:1 (i.e., the nucleotide sequence of PvGrx5). (All integers between 80% and 100% are also considered to be within the scope of the present invention with respect to percent identity.)

Furthermore, the present invention also encompasses use of fragments and derivatives of the nucleotide sequence of SEQ ID NO:1 (FIG. 1), as well as of the sequences from other sources, and having the above-described complementarity or correspondence. Functional equivalents of the above-sequences (i.e., sequences having glutaredoxin activity) are also encompassed by the present invention.

The invention also includes a purified polypeptide which has glutaredoxin activity and has at least about 80% amino acid similarity or identity, preferably at least about 85% similarity or identity, more preferably at least about 90% similarity or identity, and most preferably at least about 95% similarity or identity to the amino acid sequence (i.e., SEQ ID NO:2, see FIG. 1)] of the above-noted proteins which are, in turn, encoded by the above-described nucleotide sequences. All integers between 80-100% similarity or identity are also included within the scope of the invention.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments. "Percentage of sequence identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino acid sequences is defined as the presence of a series of exactly alike or invariant amino acid residues in both sequences.)

The definitions of "complementarity", "identity" and "similarity" are well known to those of ordinary skill in the art.

Encoded by" refers to a nucleic acid sequence which codes for a polypeptide sequence, wherein the polypeptide sequence or a portion thereof contains an amino acid sequence of at least 3 amino acid residues, more preferably at least 8 amino acid residues, and even more preferably at least 15 amino acid residues from a polypeptide encoded by the nucleic acid sequence.

Figure 1:
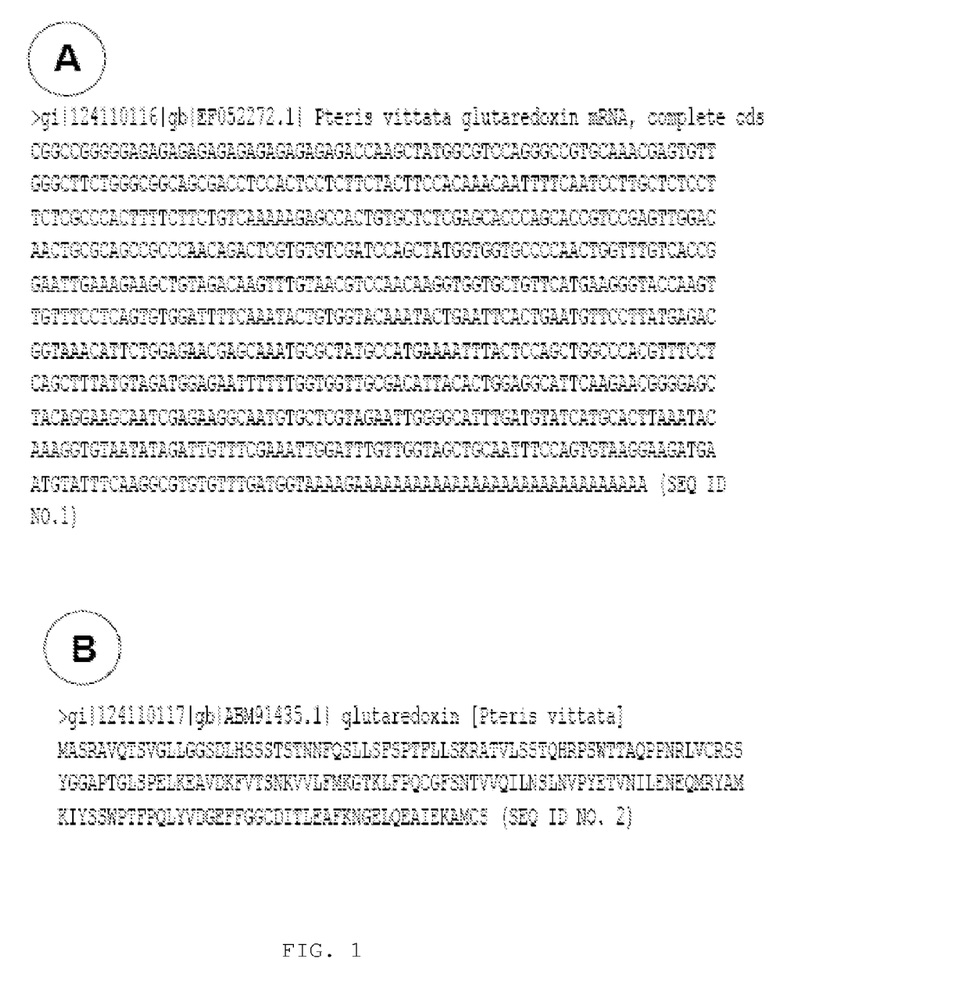
FIG. 1 shows (A) Pv5-6 cDNA sequence and (B) the deduced amino acid sequence of PvGRX5.

The present invention also encompasses an isolated nucleotide sequence which encodes PvGRX5 activity and that is hybridizable, under moderately stringent conditions, to a nucleic acid having a nucleotide sequence comprising or complementary to the nucleotide sequence comprising SEQ ID NO:1 (shown in FIG. 1). A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides 100 bp in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

The term "isolated" means separated from its natural environment. Methods, vectors, and compositions for transforming plants and plant cells in accordance with the invention are well-known to those skilled in the art, and are not particularly limited. For a descriptive example see Karimi et al., TRENDS in Plant Science, Vol. 7, No. 5, May 2002, pp. 193-195, incorporated herein by reference.

Glutaredoxins are heat-stable oxidoreductases that catalyze glutathione-dependent reactions to protect specific cellular proteins from damage by reactive oxygen species. Specifically, glutaredoxins are known to reduce disulfide bridges between proteins or reduce protein-glutathione adducts (Rouhier et al. 2008).

Glutaredoxins act by interacting with specific target proteins, altering their redox states and function. While microbes have few glutaredoxins, plants contain many glutaredoxins, with *Arabidopsis thaliana* having 31 and *Oryza sativa*. One glutaredoxin may be interacting with several target proteins and hence may influence activities of several enzymes (Rouhier et al. 2005; Li et al. 2007). The present inventors have surprisingly found that constitutive overexpression of a particular glutaredoxin, PvGRX5, from the fern *Pterris vittata* significantly increased the stress tolerance in homozygous lines of *Arabidopsis thaliana* and reduced oxidative damage to proteins of the plant.

Figure 3:
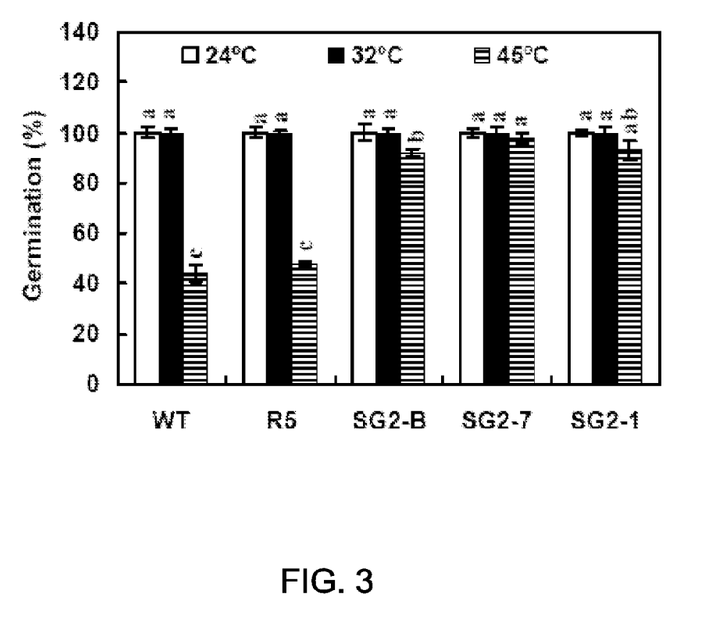
FIG. 3 shows that *Arabidopsis thaliana* transgenic lines expressing PvGrx5 are more tolerant to heat stress during seed germination. Percent germination of wild-type (WT), vector control (R5) and PvGRX5-expressing lines (SG2-B, SG2-7 and SG2-1) following control (24° C. and 32° C.) or heat stress (45° C.) treatments. Bars represent means and standard errors (n=3 batches. 50 seeds per batch for each genotype) and those noted with same letters are not significantly different at $P<0.05$ by Duncan's multiple range test.

The cDNA encoding PvGrx5 was characterized and isolated in Sundaram S, Rathinasabapathi B, Ma L, Rosen B, An Arsenate-activated Glutaredoxin from the Arsenic Hyperaccumulator Fern *Pterris vitatta* L. Regulates Intracellular Arsenite, J. of Biol. Chem. 281:10, 2008, 6095-6101 (Sundaram 2008), the entirety of which is incorporated by reference. Furthermore, PvGrx5 is shown as being a 184-residue polypeptide with a sequence (SEQ ID NO. 1) as set forth in FIG. 3 of Sundaram 2008.

In accordance with one aspect of the present invention, there is provided a method for increasing stress resistance in a plant by reducing protein carbonylationoxidative damage to plant proteins.

In accordance with one aspect of the present invention, there is provided a method for increasing the stress tolerance of plant cells comprising expressing PvGrx5 in the plant cells.

In accordance with yet another aspect of the present invention, there is a provided a method for increasing the tolerance of a plant to high temperature stress and drought, and for reducing oxidative damage to plants proteins of the plant, comprising introducing a nucleic acid that encodes for PvGrx5 into a plant cell of the plant and transforming the plant cell with the nucleic acid that encodes for PvGrx5.

In accordance with yet another aspect of the present invention, there is provided a method for producing PvGrx5 comprising: culturing host cells, wherein the cells have been transformed with a nucleic acid encoding PvGrx5 under conditions where the PvGrx5 is expressed, and isolating the PvGrx5.

In accordance with yet another aspect of the present invention, there is provided a particular method for increasing the biomass yield in plants comprising expressing PvGrx5 in the plants.

In accordance with yet another aspect of the present invention, there is provided an isolated and purified PvGrx5 product having the amino acid sequence of SEQ ID NO: 1 (FIG. 1).

In accordance with yet another aspect of the present invention, there is provided a method of producing the PvGrx5 described above, comprising culturing host cells that have been transformed with a nucleic acid encoding the PvGrx5 under conditions in which the PvGrx5 is expressed, and isolating the PvGrx5.

In an embodiment, in any of the above methods, the plant or plant cells comprise *Arabidopsis thaliana* or plant cells of *Arabidopsis thaliana* that constitutively express PvGrx5.

In an embodiment, PvGrx5 could be overexpressed in a particular organelle (for example in the plastids) to realize increased functional protein, stress tolerance or yield. Methods to overexpress cDNAs or genes via organellar transformation are available in prior art.

In addition, in any embodiment of any of the above-described methods, the plant or plant cells have increased resistance to high temperature stress and drought. In this way, the present invention thus provides crop varieties that perform better under adverse conditions. For example, cultivars with improved drought and heat tolerance will contribute to sustainability by decreasing the demand on irrigation, for example. In addition, the above-described methods may also increase the biomass or size of a plant. Further, by increasing plant leaf biomass may increase the yield of leafy vegetables for human or animal consumption. Additionally, increasing leaf biomass can be used to increase production of plant-derived pharmaceutical or industrial products. Further, by increasing plant biomass, increased production levels of the products may be obtained from the plants.

Furthermore, the increased biomass may increase crop yields of plants by increasing total plant photosynthesis. An increase in total plant photosynthesis is typically achieved by increasing leaf area of the plant. Additional photosynthetic capacity may be used to increase the yield derived from particular plant tissue, including the leaves, roots, fruits or seed. In addition, the ability to modify the biomass of the leaves may be useful for permitting the growth of a plant under decreased light intensity or under high light intensity. Modification of the biomass of another tissue, such as roots, may be useful to improve a plant's ability to grow under harsh environmental conditions, including drought or nutrient deprivation, because the roots may grow deeper into the ground. Increased biomass can also be a consequence of some strategies for increased tolerance to stresses, such as drought stress. Early in a stress response, plant growth (e.g., expansion of lateral organs, increase in stem girth, etc.) can be slowed to enable the plant to activate adaptive responses. Growth rate that is less sensitive to stress-induced control can result in enhanced plant size, particularly later in development. See U.S. Patent Publication No. 2004/0128712 which is incorporated herein by reference.

The following examples set forth an exemplary embodiment of the present invention, wherein a cDNA for the glutaredoxin PvGrx5 is introduced into homozygous lines of the *Arabidopsis thaliana* plant shows substantially increased resistance to high temperature stress and drought, along with increased resistance to oxidative damage to proteins of the cell. However, one skilled in the art would understand that the illustration of the invention in *Arabidopsis thaliana* is merely exemplary, and is not intended to be limiting to such plants. As set forth below and in the figures, the inventors have found that the transgenic expression of fern *Pteris vittata* glutaredoxin (PvGrx5) in homozygous lines of the *Arabidopsis thaliana* plant significantly increases the plant's tolerance to stress and reduces oxidative damage to the plant's proteins. In particular, plants, i.e. *Arabidopsis thaliana*, transgencially expressing PvGrx5 are less affected by high temperature stress, for example, as judged by germination during heat stress (FIG. 3), growth under heat stress (FIGS. 4A and 4B and FIG. 5), ion leakage (FIG. 6A), protein carbonyl content (FIG. 6C) and TBARS concentration (FIG. 6B) following heat stress, consistent with a role for PvGrx5 in protecting photosynthesis, membrane integrity and proteins against damage by ROS.

Figure 6:
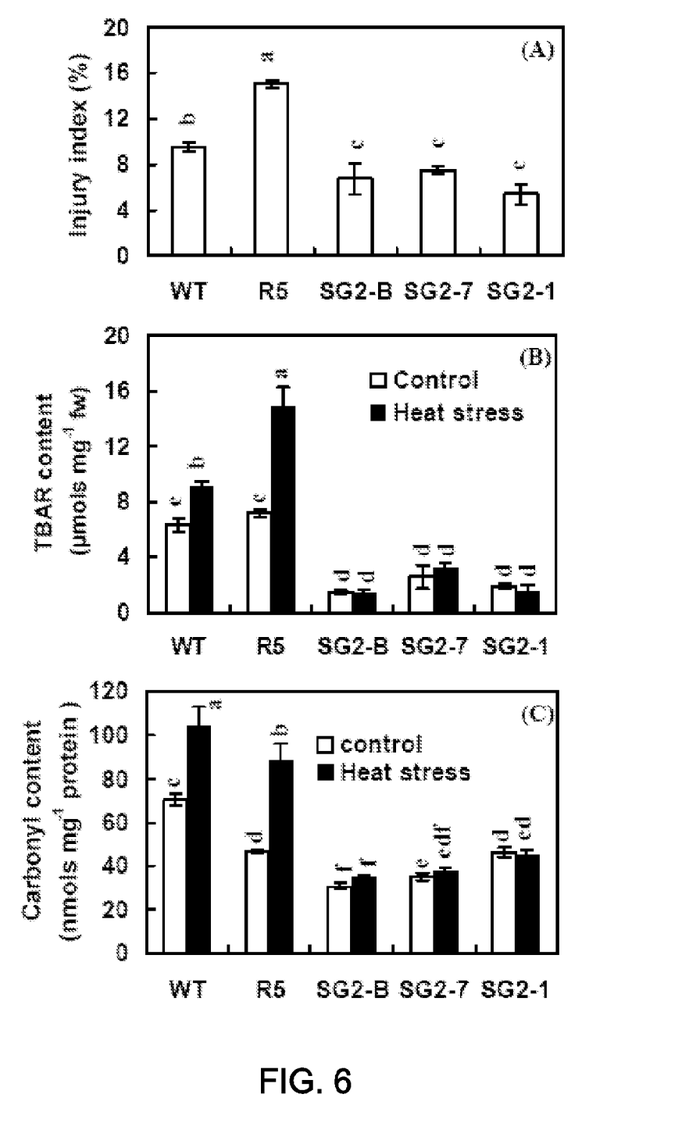
Figure 7:
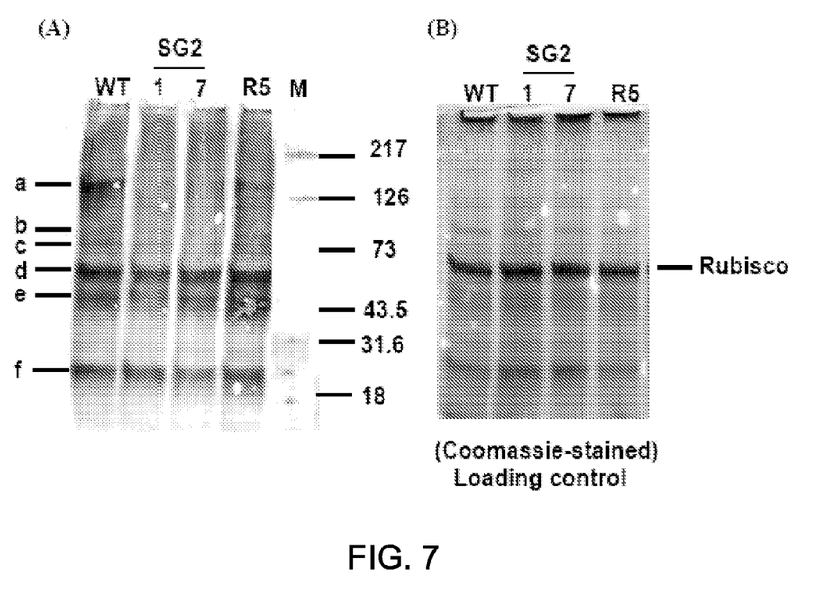
FIG. 7 shows PvGrx5-expressing *Arabidopsis thaliana* lines were less affected for oxidative damage to proteins. Immunoblot analysis for carbonylated proteins. (A) Immunoblot of total leaf proteins from heat-stressed plants, probed with anti-DNP antibodies. Protein bands differentially stained between the control (WT and R5) and SG2 lines (1 and 7 for SG2-1 and SG2-7) are shown with arrows a, b, c, d, e and f. Protein molecular weight standards are shown in lane M. (B) SDS-PAGE Gel stained with Coomasie Blue to show equal loading of the lanes. The position of the band corresponding to RUBISCO large subunit is shown with an arrow. WT is wild-type, R5 vector control and 1 and 7 are SG2-1 and SG2-7 lines respectively.

Further, based on the below examples, it is believed that PvGrx5 interacts with one or more proteins sensitive to oxidative damage to prevent oxidative damage to the proteins. Johansson et al. (2004) identified HSP70, OEC33, Rubisco large subunit, Rubisco-activase, and chlorophyll a/b binding protein, for example, to be most sensitive to oxidation in *Arabidopsis thaliana*. Among these, HSP70, which is under redox-dependent regulation by thioredoxin (Vignols et al., 2003), and Rubisco-activase have been demonstrated to play major roles in heat stress tolerance (Lee and Vierling, 2000; Kurek et al. 2007; Salvucci, 2008). Immunoblot analyses showed that specific proteins in SG2 lines of *Arabidopsis thaliana* are protected from carbonylation during heat stress (FIG. 7). The protein bands positioned at 149, 100, 70, 60, 49 and 23 kDa showed significant differences in the extent of carbonylation between the SG2 lines analyzed and the wild-type and vector control (FIG. 6A and 6B). A quantitative analysis of protein bands for carbonylation in wild-type and SG2 line indicated that protein bands at or around 149 kDa and 100 kDa were most completely protected by PvGRX5 overexpression (a reduction of 57±4%, n=3) while partial protection was observed for proteins at or around 70, 60, 49 and 23 kDa with reductions in carbonylation estimated at 44, 25, 20 and 23%.

Thus, it is believed that PvGrx5 interacts with HSP70, OEC33, Rubisco large subunit, Rubisco-activase, and chlorophyll a/b binding protein, and possibly other proteins to protect the proteins from irreversible oxidative damage directly or indirectly by PvGrx5.

EXAMPLE 1

Plant Material
Construction of Expression Vector and *Agrobacterium*-mediated Transformation.

The construction of expression vector and *Agrobacterium*-mediated transformation were done as described previously (Sundaram et al., 2009). Briefly, the open reading frame (726 bp) of the Pv5-6 cDNA clone (Genbank accession number EF052272) was amplified and the PCR product, cloned in pCR 2.-1-TOPO vector. TOPO-PvGrx5 was digested with SacI and cloned in SacI-linearized plant expression vector pMON-R5 (Fouad and Rathinasabapathi, 2006) to derive pMON-R5-SG2. pMON-R5 vector allows constitutive expression of cDNAs under the control of a modified Fig Mosaic Virus promoter and contains a kanamycin resistance marker (Fouad and Rathinasabapathi, 2006). The pMON-R5-SG2 and pMON-R5 were transferred into *Agrobacterium tumefaciens* ABI strain via triparental mating (An et al., 1988). Plants were inoculated with *A. tumefaciens* strain (ABI) carrying pMON-R5-SG2 or pMON-R5 by the floral dip method (Clough and Bent, 1998). Presence of the transgene in primary transgenics was verified using a PCR procedure on isolated genomic DNA as a template with PvGrx5 gene specific primers. The positive plants were grown in controlled environments and the seeds were collected from individual plants. From the T2 seeds, segregating for the transgene 3:1, several plants were selfed and their progeny analyzed for homozygozity. Homozygous T3 lines identified from these analyses were used for evaluations of transgene expression (Sundaram et al., 2009) and heat stress tolerance.

EXAMPLE 2

Phenotypic Characterization for Heat Tolerance
To evaluate heat tolerance during germination, seed germination assay was performed according to Hong and Vierling (2000). Surface-sterilized seeds were treated at 24° C. and 45° C. for 60 min and plated on 0.5×MS medium containing 0.5% (w/v) sucrose, and kept at 4° C. for a minimum of 48 hours and then moved to 24° C. for three days. Germinated seeds were counted to calculate percent germination.

To evaluate whole plant tolerance to heat stress, plants were grown individually in 3-inch plastic containers, using a commercial propagation medium (Mix number 2, Fafard Inc., Agawam, Mass.) (a peat moss, perlite, and vermiculite mixture). The plants were grown under 16-h-light photoperiod of 150 μmol sec($^-1$)m($^2$) supplied by cool white fluorescent lights at 24° C. constant temperature. A heat tolerance assay was performed by incubating one month old seedlings continuously at 36° C. (without changing light intensity and maintaining relative humidity between 60 and 70%) for 3 days (heat stress), followed by 10 days recovery by keeping the heat-stressed plants at 24° C. Fresh and dry weights of above-ground biomass was recorded either at the end of the stress period or the recovery period.

Under normal growth conditions, PvGrx5-expressing lines and vector control lines were comparable in growth (FIG. 1A and FIG. 1B). Development and seed set were normal except that the SG2 lines bolted 2-3 days earlier than the wild-type or vector control (data not shown). To evaluate high temperature stress tolerance, one month old plants initially grown at 25° C. were incubated in an environmental growth chamber set at 36° C. and 60-70% relative humidity for three days. To evaluate recovery from heat stress, one set of plants were moved to 24° C. for 10 days immediately after the heat stress treatment. Above ground biomass data showed that under stress, SG2 lines grew significantly (P<0.05) better than the vector control line (FIG. 1B). Whereas the vector control line was inhibited by the heat stress, the SG2 lines were not significantly inhibited (FIG. 1B).

EXAMPLE 3

Ion Leakage Test

To measure the ion leakage caused by high temperature stress, the leaves were removed from the plants, weighed, rinsed briefly with deionized water, and immediately immersed in a vial with 10-mL of deionized water. Samples were kept in an incubator shaker for 1 hour at 25° C., and ion leakage into the water was measured using a conductance bridge (Model 31A, YSI Inc., Yellow Springs, Ohio, USA). Samples were then autoclaved for 5 min, and then kept in the shaker for 1 hour at 25° C. and conductivity was measured again. With the two measurements, percent injury index was determined using the equation $1-[(1-T1/T2))/(1-C1/C2)] \times 100\%$, wherein T1 and T2 represent conductivity values for heat-stressed plants before and after autoclaving, and wherein C1 and C2 represent conductivity values for control plants before and after autoclaving (Kocheva et al. 2004). Ion leakage measurements on leaves from heat-stressed plants showed that SG2 lines exhibited significantly (P<0.05) less ion leakage than the vector control line (FIG. 6).

EXAMPLE 4

Chlorophyll Fluorescence Measurement

Figure 4:
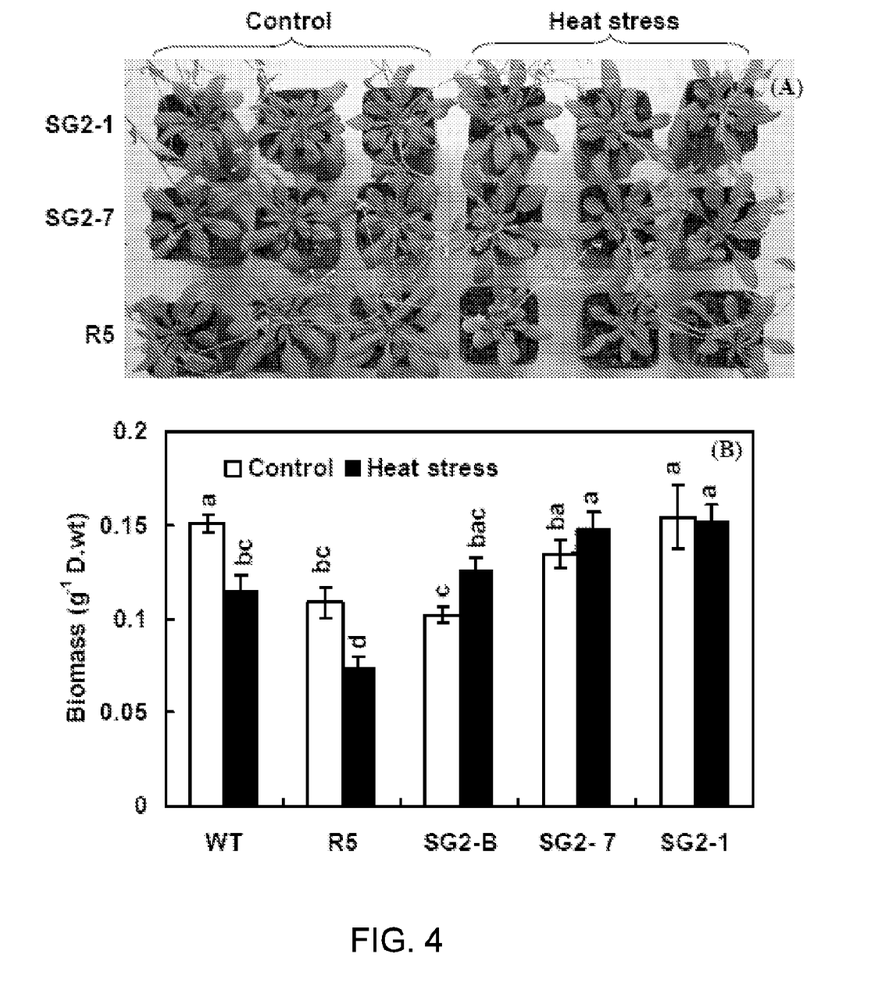
FIG. 4 shows that *Arabidopsis thaliana* transgenic lines expressing PvGrx5 are more tolerant to heat stress. (A) Phenotype of one-month old vector control (R5) and PvGRX5-expressing lines (SG2-1 and SG2-7) following control (24° C.) or photographed immediately after continuous heat stress (36° C.) for three days. (B) Above-ground biomass of wild-type (WT), vector control (R5), and PvGRX5-expressing lines (SG2-B, SG2-7 and SG2-1) following three days of control (24° C.) (open bars) or heat stress (36° C.) (closed bars). Bars represent means and standard errors (n=10) and those noted with same letters are not significantly different at $P<0.05$ by Duncan's multiple range test.
Figure 5:
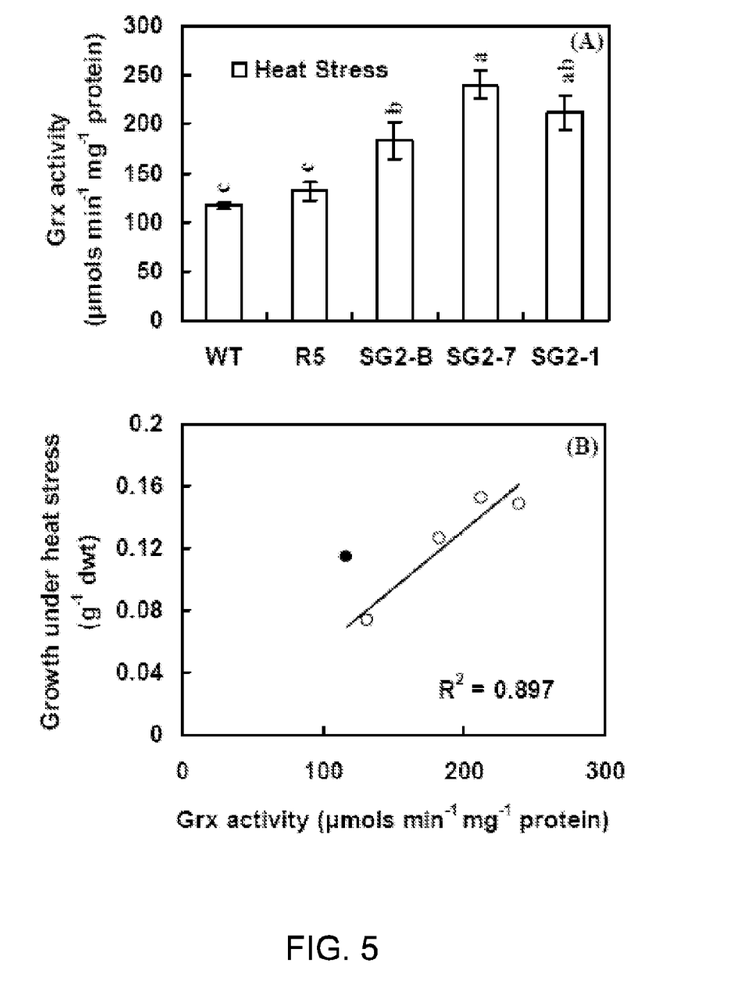
FIG. 5 shows that leaf glutaredoxin specific activities are positively correlated to plant growth under stress. Leaf glutaredoxin specific activities under stress are positively correlated to plant growth under stress. (A) Leaf glutaredoxins specific activities in wild-type (WT), vector-control (R5) and PvGRX5-expressing *Arabidopsis thaliana* transgenic lines (SG2B, SG2-7 and SG2-1). Bars represent means and standard errors (n=10) and those noted with same letters are not significantly different at $P<0.05$ by Duncan's multiple range test. (B) Relationship between leaf glutaredoxin specific activities and growth under heat stress. One outlier, (data for the wild-type) not included in the regression is shown with a closed circle.
Figure 8:
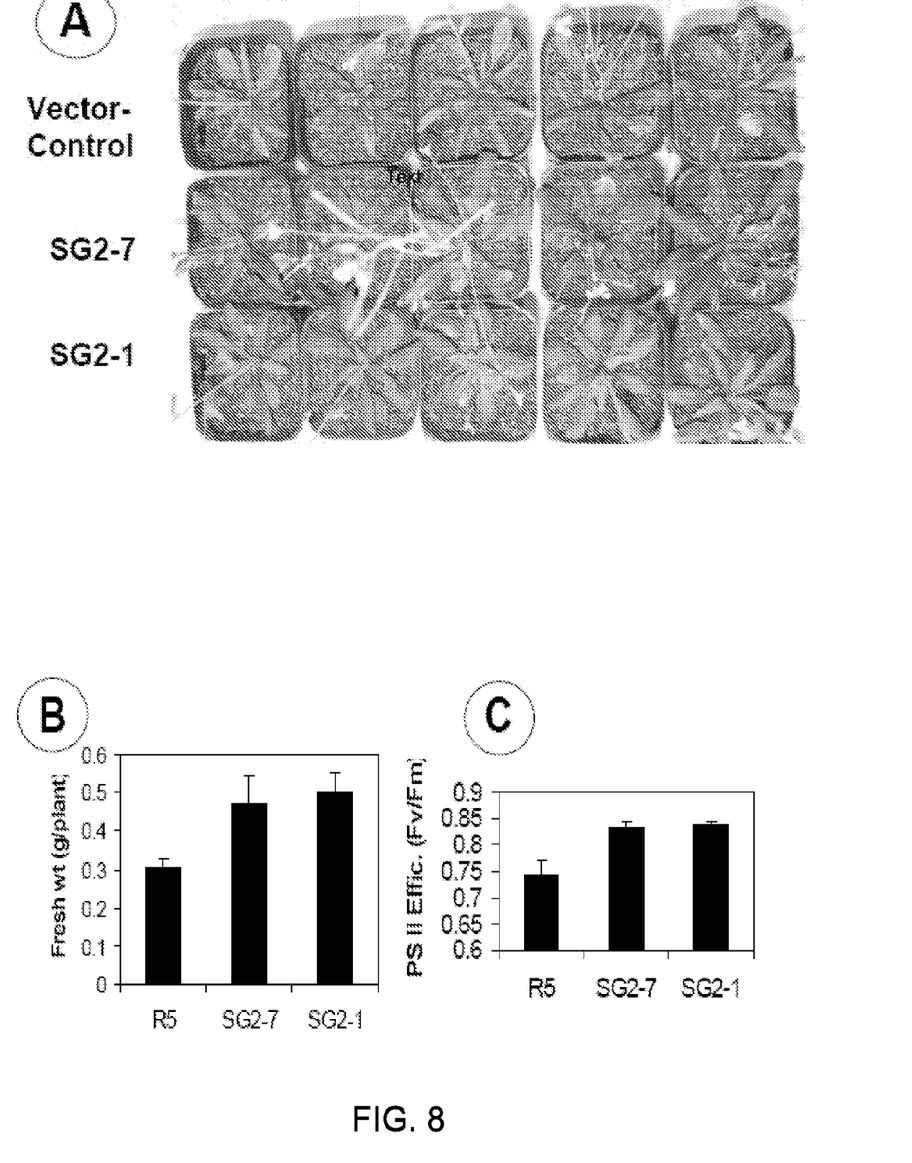

PSII photosynthesis efficiency was measured by recording the chlorophyll fluorescence parameter Fv/Fm with the Plant Efficiency Analyzer (Hansatech Instrument, King,s Lynn, UK). Leaves were dark adapted for 10 min, and then measurements were taken over a 5 second interval after exposure at the 100% illumination level by high-intensity light emitting diodes. Seven replicates from different plants were averaged for each data point. Chlorophyll fluorescence measurements (Fv/Fm) were comparable at 0.84±0.2 among the lines under no stress, control conditions (FIG. 4A). Under heat stress, all the lines showed a slight decrease (about 10%), but the vector control line was significantly more affected than the SG2 lines (FIG. 8).

EXAMPLE 5

Glutaredoxin Assay

Figure 2:
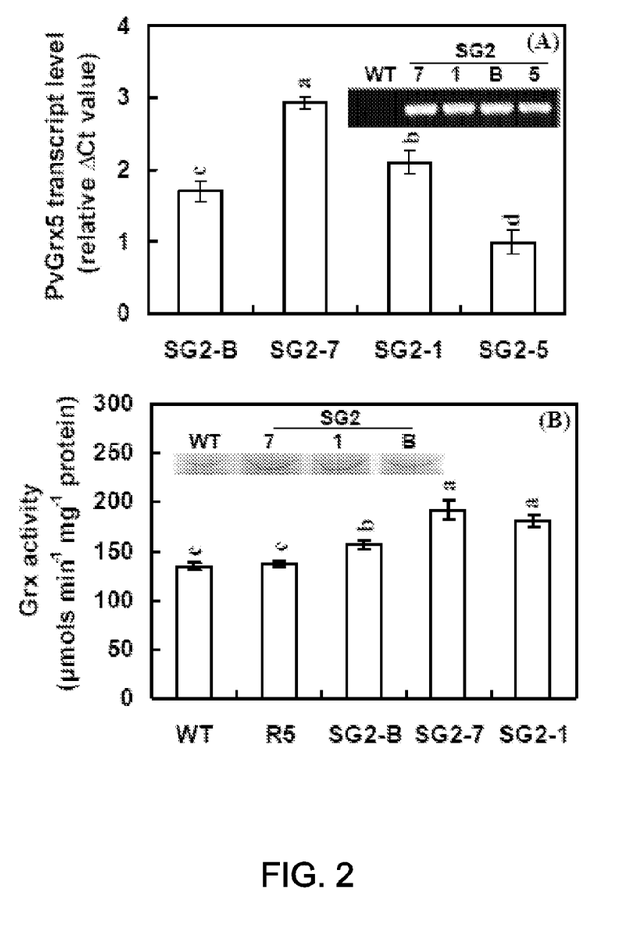
FIG. 2 shows evidence for the presence of the transgene and its expression in *Arabidopsis thaliana* transgenic lines. (A) PvGrx5 transcript levels were measured by quantitative RT-PCR. Inset: PCR amplification of PvGrx5 using genomic DNA as a template from the SG2 lines and wild-type (WT). (B) Extractable gluaredoxin specific activities from leaves of SG2 lines and vector control (R5) and wild-type (WT) lines grown under control (no-stress) conditions. Bars representing means and standard errors, marked with the same letter are not significantly different using Duncan's multiple range test ($P \leq 0.05$). Inset: Immunoblot showing a protein band at 20 kDa for wild-type control (WT) and SG2 lines (7, 1 and B).

Glutaredoxin activity in leaf protein extracts was determined with a coupled enzyme reaction as described previously (Sundaram et al. 2008a) using 2-hydroxyethyl disulfide (HED) as the substrate. In heat-stressed plants, glutaredoxin specific activities in leaf protein extracts were significantly greater than the vector control line and wild-type (FIG. 2B) and were positively correlated to growth under heat stress ($R2=0.0.89$) (FIGS. 5A and 5B).

EXAMPLE 6

Determination of Lipid Peroxidation

Lipid peroxidation in the leaves was quantified with the thiobarbituric acid (TBA) test, which determines the malondialdehyde (MDA) and related products as an end product of lipid peroxidation (Hodges et al. 1999). Leaves (200 mg) were homogenized in 2 mL of 0.1% (w/v) ice cold trichloroacetic acid (TCA). Thereafter, the homogenate was centrifuged at 12,000 g for 15 minutes. To the 0.4 mL of the supernatant, 0.8 mL of 0.5% (w/v) TBA in 20% (w/v) TCA was added. The mixture was incubated in boiling water bath for 30 minutes, and the reaction was stopped by incubating in ice. Samples were centrifuged at 10,000 g for 10 min. and the absorbance was measured at 532 nm. Then subtracting the value for non specific absorption at 600nm, the amount of MDA-TBA complex was calculated from the extinction co-efficient 155 $mm^{-1} cm^{-1}$.

EXAMPLE 7

Determination of Carbonyl Content

The carbonyl groups in proteins were determined spectrophotometrically using the dinitrophenyl hydrazine (DNPH) method (Levine et al. 1994). Total soluble proteins (0.5 mg) were incubated with the 1% (w/v) streptomycin sulfate and 0.3% (v/v) Trion x-100 for 20 min to remove the nucleic acids and centrifuged at 2000 g for 20 minutes. To the supernatant (200 μL) were 12 mixed 300 μL of 10 mM DNPH in 2M HCl. For blanks, the supernatants were mixed with 300 μL of 2M HCl. The mixture was incubated at room temperature for 1 hour, and then the protein was precipitated by adding 10% (w/v) trichloroacetic acid. The pellets were washed thoroughly using ethanol: ethyl acetate (1:1). The final pellets were dissolved using 6M guanidine hydrochloride in 20 mM potassium phosphate at pH 2.3, and the absorption was measured at 370 nm. The protein recovery was estimated by measuring the absorbance at 280 nm. The carbonyl content was calculated using the molar absorption co-efficient for aliphatic hydrazones of 22,000 M($^-1$)cm($^-1$).

To evaluate the extent of oxidative stress, carbonyl contents in soluble proteins and thiobarbituric acid-reactive substances (TBARS) were measured from plants exposed to heat stress and control conditions. Under control conditions, carbonylated protein contents were significantly less (P<0.05) in SG2 lines than the vector control and wild-type (FIG. 5A). Under stress, the protein carbonyl content significantly (P<0.05) increased in both vector control line and wild-type, but not in SG2 lines (FIG. 5B). TBARS in leaves, an index of lipid peroxidation, also showed that even under control conditions, SG2 lines had significantly (P<0.05) lower TBARS than vector control and wild-type. Under stress, the TBARS in wild-type and vector controls significantly increased, but not in SG2 lines (FIG. 5B).

EXAMPLE 8

Detection of Carbonylated Protein

The carbonyl groups in the proteins were derivatized using DNPH (Srivalli and Khanna Chopra, 2004). Total soluble protein (10 μg) were mixed with an equal volume of 12% sodium dodecyl sulfate (SDS) and then with two volumes of 20 mM DNPH dissolved in 10% trifluoroacetic acid (TFA). For 2 controls, the samples were treated only with 10% TFA. The mixture was incubated for 25 minutes at room temperature and the reaction was stopped by adding 1.5 sample volumes of 2M Tris containing 30% (v/v) glycerol. The volumes mentioned above, refer to the volume of the sample, before the addition of the DNPH. The samples were loaded onto an 8-16% SDS-PAGE (Laemmli, 1970). Then, the proteins were electrotransferred onto a PVDF membrane (Biorad, Richmond, Calif., USA) at 40° C. at 100V for 90 min. The blot was incubated with primary antibody, rabbit anti-DNP with the titer of 1:2000 (Sigma-Aldrich Co) and immunoreactive proteins were visualized using anti-rabbit IgG alkaline phosphate conjugated antiserum with 5-bromo-4-chloro-3-indolyl phosphate/nitroblue tetrazolium substrate (Sigma-Aldrich Co). The molecular weights of protein bands for oxidatively-damaged proteins were calculated using the Rf value.

To identify proteins that may be protected from carbonylation, immunoblots were used and probed with anti-DNP antibody. Following loading of equal amounts of leaf total proteins, protein bands positioned at The protein bands positioned at 149, 100, 70, 60, 49 and 23 kDa showed significant differences in the extent of carbonylation between the SG2 lines analyzed and the wild-type and vector control (FIG. 7). This data suggests the SG2 lines are protected from irreversible oxidative damage directly or indirectly by PvGrx5.

EXAMPLE 9

To evaluate drought tolerance of PvGRX5-expressing lines, PvGRX5-lines and control lines were grown individually in 3-inch plastic containers, using a commercial propagation medium (Mix number 2, Fafard Inc., Agawam, Mass.). The plants were grown under 16-h-light photoperiod of 150 μmol sec$^{-1}$ m$^2$ supplied by cool white fluorescent lights at 24±1° C. constant temperature and 70% RH. They were watered every alternate day to container capacity via sub-irrigation in containers which were irrigated with 20 mL of half-strength Hoagland nutrient medium each time. After one month of growth, for a set of plants, drought stress treatment was imposed by withholding water for 10 days. At the end of the drought period, the plants were photographed and PSII efficiency and above ground biomass were recorded (FIG. 8).

References

Cheng NH, Liu JZ, Brock A, Nelson RS, Hirschi KD (2006) AtGRXcp, an *Arabidopsis* chloroplastic glutaredoxin, is critical for protection against protein oxidative damage. J Biol Chem 281: 26280-26288.

Davison PM, Hunter CN, Horton P (2002) Overexpression of beta-carotene hydroxylase enhances stress tolerance in *Arabidopsis*. Nature 418: 203-206.

Fouad WM, Rathinasabapathi B (2006) Expression of bacterial L-aspartate-alpha-decarboxylase in tobacco increases beta-alanine and pantothenate levels and improves thermotolerance. Plant Mol Biol 60: 495-505.

Grant CM, Luikenhuis S, Beckhouse A, Soderbergh M, Dawes IW (2000) Differential regulation of glutaredoxin gene expression in response to stress conditions in the yeast *Saccharomyces cerevisiae*. Biochim Biophys Acta 1490: 33-42.

Hodges MD, DeLong JM, Forney CF, Prange RK (1999) Improving the thiobarbituric acidreactive-substances assay for estimating lipid peroxidation in plant tissues containing anthocyanin and other interfering compounds. Planta 207: 604-611.

Hong SW, Vierling E (2000) Mutants of *Arabidopsis thaliana* defective in the acquisition of tolerance to high temperature stress. Proc Natl Acad Sci USA 97: 4392-4397.

Johansson E, Olsson O, Nystrom T (2004) Progression and specificity of protein oxidation in the life cycle of *Arabidopsis thaliana*. J Biol Chem 279:22204-22208.

Katiyar-Agarwal S, Agarwal M, Grover A (2003) Heat-tolerant basmati rice engineered by over-expression of hsp101. Plant Mol Biol 51:677-686.

Klatt P, Lamas S (2000) Regulation of protein function by S-glutathionylation in response to oxidative and nitrosative stress. Eur J Biochem 267: 4928-4944.

Kocheva K, Lambrev P, Georgiev G, Goltsev V, Karabaliev M (2004) Evaluation of chlorophyll fluorescence and membrane injury in the leaves of barley cultivars under osmotic stress. Bioelectrochem 63:121-124.

Koskull-Doring P, Scharf K, Nover L (2007) The diversity of plant heat stress transcription factors. Trends in Plant Sci 12:452-457.

Kotak S, Larkindale J, Lee U, Koskull-Doring P, Vierling E, Scharf K (2007) Complexity of the heat stress response in plants. Curr Opion Plant Biol 10:310-316.

Kurek I, Chang TK, Bertain SM, Madrigal A, Liu L, Lassner MW, Zhu G (2007) Enhanced thermostability of *Arabidopsis* Rubisco activase improves photosynthesis and growth rates under moderate heat stress. Plant Cell 19:3230-3241.

Laemmli UK (1970) Cleavage of structural proteins during the assembly of the head of the bacteriophage T4. Nature 227: 680-685

Lee JH, Hubel A, Schoffl F (1995) Derepression of the activity of genetically engineered heat shock factor causes constitutive synthesis of heat shock proteins and increased thermotolerance in transgenic *Arabidopsis*. Plant J8: 603-612

Lee GJ, Vierling E (2000) A small heat shock protein cooperates with heat shock protein 70 systems to reactivate a heat-denatured protein. Plant Physiol 122:189-198

Levine RL, Williams JA, Stadtman ER, Shacter E (1994) Carbonyl assays for determination of oxidatively modified proteins. Methods Enzymol. 233:346-357.

Li M, Yang Q, Zhang L, Li H, Cui Y, Wu Q (2007) Identification of novel targets of cynobacterial glutaredoxin. Arch Biochem Biophys 458:220-228.

Lobell DB, Field D B (2007) Global scale climate-crop yield relationships and the impacts of recent warming. Environ Res Lett 2:014002.

Mittler R (2005) Abiotic stress, the field environment and stress combination. Trends in Plant Sci 11:15-19.

Rathinasabapathi B, Kaur R (2006) Metabolic engineering for stress tolerance. In: Rao K V M, Rahavendra A S, Reddy KJ (eds), Springer, Dordrecht, The Netherlands, pp 255-299.

Rodriguez-Manzaneque MT, Ros J, Cabiscol E, Sorribas A, Herrero E (1999) Grx5 glutaredoxin plays a central role in protection against protein oxidative damage in *Saccharomyces cerevisiae*. Mol Cell Biol 19:8180-8190.

Ross T, Lott N (2003) A climatology of 1980-2003 extreme weather and climate events. US Department of Commerce, NOAA/NESDIS. Technical Report 2003-01.

Rouhier N, Lemaire SD, Jacquot JP. (2008) The role of glutathione in photosynthetic organisms: Emerging functions for glutaredoxins and glutahionylation. Annu Rev Plant Biol 59:143-166

Rouhier N, Couturier J, Jacquot JP. (2006) Genome-wide analysis of plant glutaredoxin systems. J Exp Bot. 2006;57 (8):1685-96

Rouhier N, Villarejo A, Srivastava M, Gelhaye E, Keech O, Droux M, Finkemeier I, Samuelsson G, Dietz KJ, Jacquot JP, Wingsle G (2005) Identification of plant glutaredoxin targets. Antioxidants & Redox Signaling 7:919-929.

Sharkey T (2005) Effects of moderate heat stress on photosynthesis: importance of thylakoid reactions, rubisco deactivation, reactive oxygen species, and thermotolerance provided by isoprene. Plant Cell Environ 28: 269-277.

Srivalli B, Khanna-Chopra R (2004) The developing reproductive 'sink' induces oxidative stress to mediate nitrogen mobilization during monocarpic senescence in wheat. Biochem Biophys Res Com 325: 198-202.

Sundaram S., Rathinasabapathi B., Ma L.Q., Rosen B. P. (2008a) An arsenate-activated glutaredoxin from the arsenic hyperaccumulator fern *Pteris vittata* L. regulates intracellular arsenite. J Biol Chem 283: 6095-6101.

Sundaram S, Wu S, Ma LQ, Rathinasabapathi B (2008b). Expression of a *Pteris vittata* glutaredoxin PvGrx5 in transgenic *Arabidopsis thaliana* increases plant arsenic resistance and decreases arsenic accumulation in the leaves. New Phytologist (Submitted).

Vacca RA, Concentta de Pinto M, Valenti D, Passarella S, Marra E, Gara L (2004) Production of reactive oxygen species, alteration of cytosolic ascorbate peroxidase, and impairment of mitochondrial metabolism are early events in heat shock-induced programmed cell death in tobacco Bright-Yellow 2 cells. Plant Physiol 134:11001112.

Vignols F, Mouaheb N, Thomas D, Meyer Y (2003) Redox control of Hsp70-Co-chaperone interaction revealed by expression of a thioredoxin-like *Arabidopsis* protein. J Biol Chem 278:4516-4523.

In the present invention, the inventors have surprisingly found that glutaredoxins could be used to manipulate post-translational modifications of thiol proteins to achieve stress-tolerant phenotypes. Glutaredoxins are known to reduce disulfide bridges between proteins or reduce protein-glutathione adducts (Rouhier et al. 2008). The functional roles for post-translational modifications of thiol proteins by glutathionylation are not completely understood. With a multitude of glutaredoxins and their possible redox controls of many target proteins, modulating the plant 'glutaredoxome' provides a powerful biotechnological tool to improve crop tolerance to high temperature stress, and abiotic and biotic stress tolerance generally.

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

The invention claimed is:

1. A method for increasing drought or high temperature stress tolerance in a plant and for reducing oxidative damage to plant proteins of the plant comprising expressing a heterologous nucleic acid encoding the amino acid sequence set forth in SEQ ID NO: 2 encoding PvGrx5 in the plant and selecting for plants that exhibit an increased tolerance to high temperature or drought stress compared to the plant without the heterologous nucleic acid when the plants are grown under the same conditions.

2. The method of claim 1, wherein expressing said heterologous nucleic acid increases the biomass and/or grain yield of said plant compared to the plant without the heterologous nucleic acid when the plants are grown under the same conditions.

3. A plant comprising a plurality of cells expressing the heterologous nucleic acid of claim 1.

4. A method of producing the PvGrx5 protein set forth in SEQ ID NO: 2 comprising culturing host cells that have been transformed with a nucleic acid encoding the PvGrx5 under conditions in which the PvGrx5 is expressed and isolating the PvGrx5.

5. The method of claim 1, further comprising producing a parent transgenic plant expressing a heterologous nucleic acid sequence encoding PvGrx5; isolating seeds from the parent transgenic plant; growing transgenic progeny plants from said seeds that comprise the nucleic acid sequence encoding PvGrx5; and selecting for a transgenic progeny plant comprising the heterologous nucleic acid that has a heat or drought stress tolerant phenotype and has a biomass greater than that of a plant having no expression of said nucleic acid sequence under heat or drought conditions.

* * * * *

UNITED STATES PATENT AND TRADEMARK OFFICE
CERTIFICATE OF CORRECTION

| | |
|---|---|
| PATENT NO. | : 8,519,226 B2 |
| APPLICATION NO. | : 12/996884 |
| DATED | : August 27, 2013 |
| INVENTOR(S) | : Bala Rathinasabapathi et al. |

It is certified that error appears in the above-identified patent and that said Letters Patent is hereby corrected as shown below:

In the Specification

Col. 1 lines 11-19

On Page 1 under the STATEMENT REGARDING FEDERALLY SPONSORED DEVELOPMENT section (LINES 14-18), please delete "Development for this invention was supported in part by Contract No. 2005-34135-15898, awarded by the United States Department of Agriculture (USDA-T-STAR Program). Accordingly, the United States Government may have certain rights in this invention" and insert --Development for this invention was supported in part by Contract No. 2005-34135-15898, awarded by the United States Department of Agriculture (USDA-T-STAR Program). Accordingly, the United States Government has certain rights in this invention.--

Signed and Sealed this
Fifteenth Day of July, 2014

Michelle K. Lee
*Deputy Director of the United States Patent and Trademark Office*